(12) United States Patent
Rashidi (10) Patent No.: US 11,523,920 B2
(45) Date of Patent: Dec. 13, 2022

(54) STENT WITH A SMOOTH SURFACE IN ITS EXPANDED CONFIGURATION

(71) Applicant: Keyvon Rashidi, Pepper Pike, OH (US)

(72) Inventor: Keyvon Rashidi, Pepper Pike, OH (US)

( * ) Notice: Subject to any disclaimer, the term of this patent is extended or adjusted under 35 U.S.C. 154(b) by 0 days.

(21) Appl. No.: 15/923,324

(22) Filed: Mar. 16, 2018

(65) Prior Publication Data

US 2018/0263798 A1     Sep. 20, 2018

Related U.S. Application Data

(60) Provisional application No. 62/471,961, filed on Mar. 16, 2017.

(51) Int. Cl.
| | | |
|---|---|---|
| *A61F 2/91* | (2013.01) | |
| *A61F 2/90* | (2013.01) | |
| *A61F 2/958* | (2013.01) | |

(52) U.S. Cl.
CPC .................. *A61F 2/90* (2013.01); *A61F 2/91* (2013.01); *A61F 2/958* (2013.01); *A61F 2240/001* (2013.01); *A61F 2250/001* (2013.01); *A61F 2250/0067* (2013.01)

(58) Field of Classification Search
CPC ..... A61F 2/91; A61F 2002/9522; A61F 2/958
See application file for complete search history.

(56) References Cited

U.S. PATENT DOCUMENTS

| | | | |
|---|---|---|---|
| 6,033,436 A | 3/2000 | Steinke et al. | |
| 6,258,121 B1 | 7/2001 | Yang et al. | |
| 6,273,908 B1 | 8/2001 | Ndondo-Lay | |
| 6,391,052 B2 | 5/2002 | Buirge et al. | |
| 6,805,706 B2 | 10/2004 | Solovay et al. | |
| 6,833,004 B2 | 12/2004 | Ishii et al. | |
| 6,923,828 B1 | 8/2005 | Wiktor | |
| 7,622,135 B2 | 11/2009 | Pathak et al. | |
| 8,075,609 B2 | 12/2011 | Penn et al. | |
| 8,133,269 B2 | 3/2012 | Flechsenhar et al. | |
| 8,414,635 B2 | 4/2013 | Hyodoh et al. | |
| 8,449,597 B2 | 5/2013 | Brown | |
| 8,840,657 B2 | 9/2014 | Hartley | |

(Continued)

FOREIGN PATENT DOCUMENTS

| | | |
|---|---|---|
| EP | 1 834 606 A1 | 9/2007 |
| EP | 3 275 402 A1 | 1/2018 |

*Primary Examiner* — Suba Ganesan
(74) *Attorney, Agent, or Firm* — Fay Sharpe LLP (57) ABSTRACT

A coronary stent is disclosed herein as having a lattice configuration on a generally thin-walled cylindrical tube. This particular stent is fabricated using an elongated thin-walled tubular solid that has a diameter equal to that of the final expanded configuration of the stent. In other words, the lattice configuration is cut onto the surface of the tubular solid that has a diameter substantially equal to the inner diameter of the blood vessel for which the stent is intended. The tubular lattice is then shrunk (collapsed) axisymmetrically to a new cylindrical configuration with a diameter substantially less than the blood vessel for which the stent is intended. The stent in its reduced diameter state can then be delivered to a desired site in the body via a catheter with an inflatable balloon at its distal portion. Upon the inflation of the balloon, the stent will assume its expanded, deployed configuration into the original diameter at the desired site in the body.

16 Claims, 6 Drawing Sheets

(56) References Cited

U.S. PATENT DOCUMENTS

| | | |
|---|---|---|
| 9,333,102 B2 | 5/2016 | Yachia et al. |
| 9,867,725 B2 | 1/2018 | Tieu et al. |
| 2002/0138131 A1 | 9/2002 | Solovay et al. |
| 2002/0177892 A1* | 11/2002 | Globerman ............... A61F 2/90 623/1.15 |
| 2004/0168298 A1* | 9/2004 | Dolan ...................... A61F 2/91 29/557 |
| 2007/0073379 A1* | 3/2007 | Chang ...................... A61F 2/95 623/1.12 |
| 2007/0199360 A1* | 8/2007 | Sarac ...................... A61F 2/95 72/135 |
| 2008/0288054 A1 | 11/2008 | Pulnev et al. |
| 2014/0100653 A1 | 4/2014 | Savage et al. |

\* cited by examiner

STENT WITH A SMOOTH SURFACE IN ITS EXPANDED CONFIGURATION

This application claims the priority benefit of U.S. provisional application Ser. No. 62/471,961, filed Mar. 16, 2017, the entire disclosure of which is expressly incorporated herein by reference.

BACKGROUND

This invention relates to stents. Stents disclosed in the prior art are formed by starting with a thin-walled, biocompatible metallic tube open at first and second ends. A lattice configuration is then cut through the wall of the tube forming a series of individual links or struts that are interconnected with one or more adjacent links at interconnection regions. In the stents of the prior art, before the stent is expanded, the outer surface of the tubular lattice is smooth, i.e., the inner and outer surfaces of the wall of the tube that has been cut are each defined by a separate surface of rotation having a constant radius measured from a longitudinal axis of the tube. Before the stent is expanded, the cuts in the tube wall extend through the wall thickness and separate the individual links from one another in an axial and/or circumferential direction, and the outer surfaces of the individual links all remain in and form the outer surface of the unexpanded, cut tube.

When the stents of the prior art are expanded, for example by a conventional stent-deploying balloon, the cuts in the wall of the tube are likewise expanded and form enlarged openings that extend radially through the tube wall. The enlarged openings are surrounded by the individual links that are joined together at the interconnection regions. Thus, the links joined together at the interconnection regions and separated from one another by the enlarged openings form a lattice arrangement. The links are distorted as the stent is expanded in radial and circumferential directions to the expanded (deployed) configuration or state from the contracted (delivery) configuration or state. The individual links assume an out-of-plane, twisted configuration relative to one another and relative to the interconnection regions that join the individual links together to form the lattice in the expanded state. Stated another way, outer surfaces of the individual links are no longer all located in the same curved surface and the entirety of the outer surfaces of the individual links are not all located at the same radial dimensions from the longitudinal axis of the tube when the stent is in the expanded state. The individual links have a twisted configuration as the links extend in a variety of directions from the interconnection regions, for example, the individual links extend in radial, axial, and circumferential directions that form an uneven, non-constant outer surface (as measured from the longitudinal axis of the stent) relative to one another. This out-of-plane twisting creates local blood-flow turbulences that may have adverse effects on the blood cells.

A need exists for an improved arrangement that provides a stent that has a smooth outer surface in its in-use configuration and having a diameter substantially equal to the inner lumen of the blood vessel that receives the stent, as well as still other features and benefits.

SUMMARY

An improved stent and method of forming the stent are disclosed herein.

A method of fabricating an intravascular stent includes providing a thin wall tube having a wall with an outer dimension (diameter) equal to that of a fully expanded configuration of the intravascular stent. The method further includes removing geometric patterns through the wall, and leaving an interconnected lattice. The method also includes contracting the stent to a contracted configuration having a smaller dimension (diameter) for storage, delivery, and subsequent deployment.

The contracting step includes radially reducing the stent from its fully expanded state to a substantially smaller dimension (diameter) state after the removing step to become deliverable through the vascular lumen and subsequently deployable at a desired site.

The method includes expanding the contracted configuration of the stent to its original, fully expanded outer dimension (diameter) when positioned at a desired site in the vascular lumen.

The contracting step may include placing the stent in a flexible tube and reducing the dimension of the flexible tube in order to contract the stent therein.

The contracting step may include placing the stent in a truss structure that when axially stretched, shrinks the stent in an axisymmetric, uniform fashion to its contracted configuration.

An alternative method includes forming the lattice with individual twisted links in the contracted configuration and removing the twist in the links in the expanded configuration, where upon expansion of the stent, the links assume untwisted configurations that results in a stent with a smooth outer surface in its in-use configuration.

A stent includes a body having a lattice configuration defined by links of material joined at spaced interconnection regions with openings formed between the interconnection regions. The body is configured and capable of being in (i) a collapsed, reduced diameter state or (ii) an expanded, enlarged diameter state, wherein in the expanded state, all radial outer surfaces of the links lie in an outer perimeter cylindrical surface portion of a virtual, continuous cylinder having the enlarged diameter.

In the collapsed state, at least some of radial outer surfaces of the links are located outside of an arcuate surface of an outer perimeter, cylindrical surface portion of a virtual, continuous cylinder having the reduced diameter.

The radial outer surfaces of the body links in the expanded state are dimensioned for operative engagement with an inner surface of an associated body passage.

A process of fabricating a stent includes forming a lattice arrangement that include a series of links and openings in a wall of a tubular body. The process includes providing a collapsed state of the tubular body where the links have a distorted configuration and an expanded state of the tubular body wherein the distorted configuration of the links vanishes.

The lattice may be formed in a tubular body that has a dimension that is the same as the expanded state.

The tubular body may be collapsible to a reduced dimension for delivery of the stent through an associated body passage, and the tubular body is then expandable to an enlarged dimension for securing the stent in the associated body passage.

The process may include surrounding the tubular body (the stent) in a sleeve (tool for contracting the stent) and reducing a cross-sectional dimension of the sleeve and uniformly deforming the tubular body to the reduced dimension.

The deforming step may include axisymmetrically reducing the dimension of the tubular body.

A primary advantage is reducing the prospect for creating turbulence to flow through the stent.

Another benefit resides in the ease of manufacture of the improved stent.

Still other benefits and advantages of the present disclosure will become more apparent from reading and understanding the following detailed description.

DETAILED DESCRIPTION

The following description with reference to the accompanying drawings is provided to assist in a comprehensive understanding of one or more embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. Various exemplary embodiments of the present disclosure are not limited to the specific details of different embodiments and should be construed as including all changes and/or equivalents or substitutes included in the ideas and technological scope of the appended claims. In describing the drawings, where possible similar reference numerals are used for similar elements.

The terms "include" or "may include" used in the present disclosure indicate the presence of disclosed corresponding functions, operations, elements, and the like, and do not limit additional one or more functions, operations, elements, and the like. In addition, it should be understood that the terms "include", "including", "have" or "having" used in the present disclosure are to indicate the presence of components, features, numbers, steps, operations, elements, parts, or a combination thereof described in the specification, and do not preclude the presence or addition of one or more other features, numbers, steps, operations, elements, parts, or a combination thereof.

The terms "or" or "at least one of A or/and B" used in the present disclosure include any and all combinations of words enumerated with them. For example, "A or B" or "at least one of A or/and B" mean including A, including B, or including both A and B.

Although the terms such as "first" and "second" used in the present disclosure may modify various elements of the different exemplary embodiments, these terms do not limit the corresponding elements. For example, these terms do not limit an order and/or importance of the corresponding elements, nor do these terms preclude additional elements (e.g., second, third, etc.). The terms may be used to distinguish one element from another element. For example, a first mechanical device and a second mechanical device all indicate mechanical devices and may indicate different types of mechanical devices or the same type of mechanical device. For example, a first element may be named a second element without departing from the scope of the various exemplary embodiments of the present disclosure, and similarly, a second element may be named a first element.

It will be understood that, when an element is mentioned as being "connected" or "coupled" to another element, the element may be directly connected or coupled to another element, and there may be an intervening element between the element and another element. To the contrary, it will be understood that, when an element is mentioned as being "directly connected" or "directly coupled" to another element, there is no intervening element between the element and another element.

The terms used in the various exemplary embodiments of the present disclosure are for the purpose of describing specific exemplary embodiments only and are not intended to limit various exemplary embodiments of the present disclosure. As used herein, the singular forms are intended to include the plural forms as well, unless the context clearly indicates otherwise.

All of the terms used herein including technical or scientific terms have the same meanings as those generally understood by an ordinary skilled person in the related art unless they are defined otherwise. The terms defined in a generally used dictionary should be interpreted as having the same meanings as the contextual meanings of the relevant technology and should not be interpreted as having inconsistent or exaggerated meanings unless they are clearly defined in the various exemplary embodiments.

Figure 1:
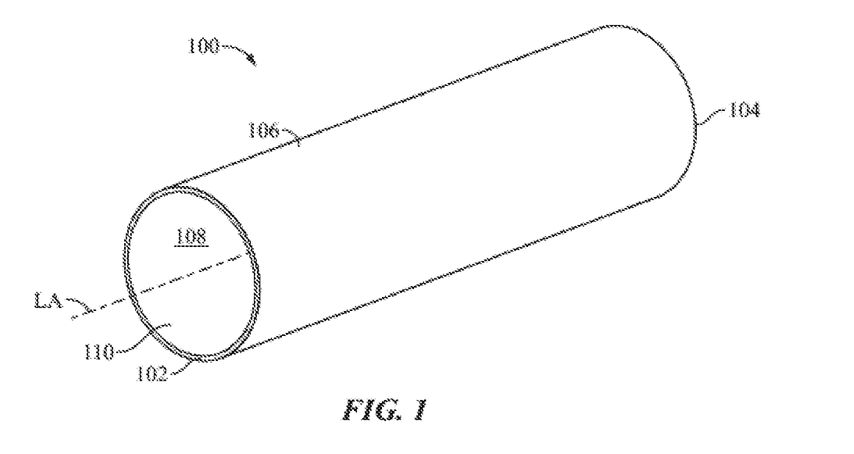
FIG. 1 is a perspective view of a thin tube from which the stent is formed according to the present invention.

FIG. 1 is an open-ended, thin walled tubular body 100 having a first or proximal end 102 and a second or distal end 104. The body 100 has a substantially cylindrical conformation where an outer surface 106 has a smooth, continuous contour defined as a surface of revolution about a longitudinal axis LA, i.e., that is equally distant from the longitudinal axis. Similarly, an inner surface 108 preferably has a smooth, continuous contour that is defined as a surface of revolution about the longitudinal axis. Thus, the inner surface 108 forms an internal through passage 110 that proceeds continuously from the open, proximal end 102 to the open, distal end 104. The body is formed of any conventional biocompatible material such as a metal e.g. stainless steel, nitinol, or the like. It will also be appreciated that the interior or exterior surfaces of the final stent may be covered with a conventional material that is used for one or more of a variety of purposes such as a drug eluting coating. The dimension of the body 100 is controlled so as to be substantially identical to the final deployed dimension of the stent, sometimes referred to herein as the expanded configuration or state of the stent. This is in contrast to the prior art arrangement where the body that was formed into a stent has a substantially smaller, first outer dimension which was then subsequently expanded to a second, enlarged outer dimension as noted in the Background.

Figure 2:
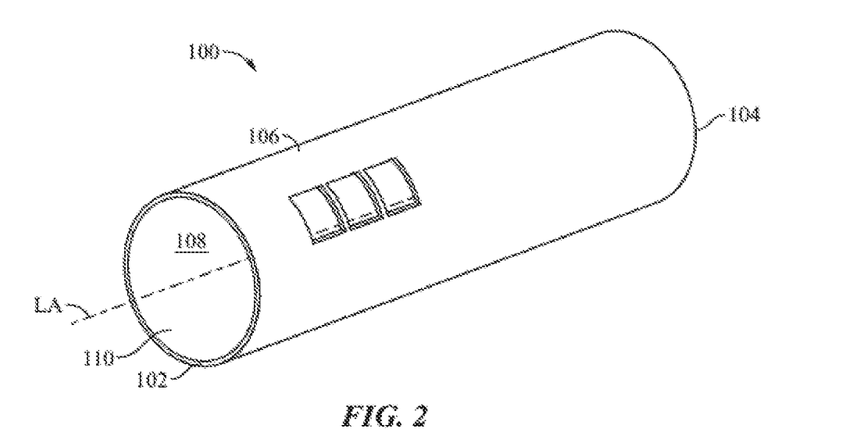
FIG. 2 is a perspective view similar to FIG. 1 illustrating a partially formed stent.
Figure 3:
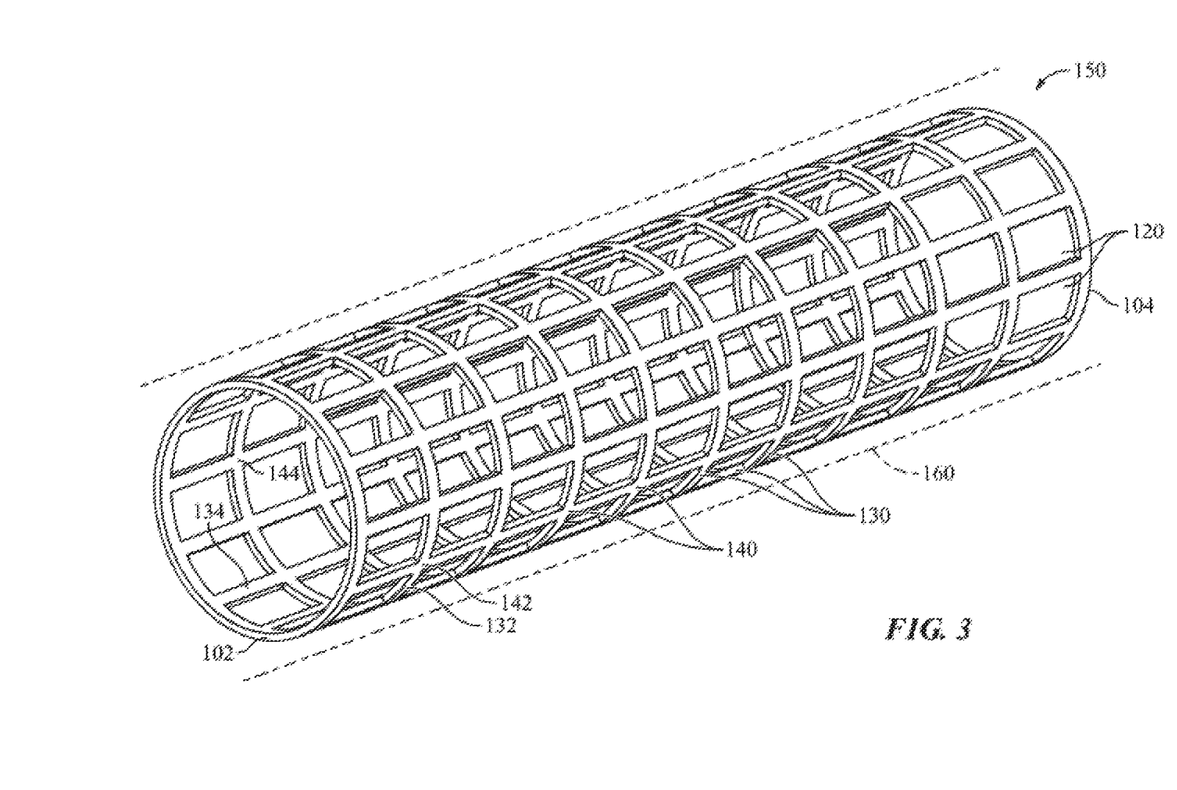
FIG. 3 is a perspective view similar to FIGS. 1 and 2 showing a fully formed stent in its expanded configuration.

With continued reference to FIG. 1, and is additionally shown in FIG. 2, openings 120 are then formed in the body 100. The openings 120 may be formed in any conventional manner, for example the openings may be etched in the body 100. The openings 120 may be regular, irregular, various configurations, etc. so that the regular, equally-spaced openings illustrated in the figures of the present application should not be deemed limiting. The openings 120 extend through the entirety of the sidewall. The openings 120 are formed in the body 100 when the body is at the same dimension as illustrated in FIG. 1, i.e., substantially identical to the final deployed dimension of the stent. As shown in FIG. 3, completion of the desired pattern of openings 120 in the body 100 defines a series of links or struts 130 (including an outer surface 132, and inner surface 134) that extend axially, circumferentially, or a combination of both axially and circumferentially. The final pattern of openings 120 and struts 130 define what is often referred to as a lattice, mesh, or metal mesh.

Where a strut 130 is joined to an adjacent strut, an interconnecting region 140 is formed. The interconnecting region 140 has an outer surface 142 and an inner surface 144. Again, any interconnecting region 140 has at least two struts 130 extending therefrom in different directions, and the particular number of struts extending toward or away from an interconnecting region 140 may vary depending on the particular design of the resulting stent 150.

As illustrated in FIG. 3, the struts 130 and the interconnecting regions 140 are located the same dimension from the longitudinal axis LA in the stent 150. This results in the smooth, outer surface 106 such that all radial outer surfaces 132 of the struts 130 lie in an outer perimeter cylindrical surface portion of a virtual, continuous cylinder having the enlarged configuration or diameter as the final deployed dimension of the stent 150. Moreover, all of the interconnecting regions 140 similarly lie in the outer perimeter cylindrical surface portion of the virtual, continuous cylinder having the enlarged configuration or diameter as the final deployed dimension of the stent 150. It is also preferred that the inner surfaces 134 of the struts 130, and likewise the inner surfaces 144 of the interconnecting regions 140, lie in the inner perimeter cylindrical surface portion of the virtual, continuous cylinder having the enlarged configuration or diameter as the final deployed dimension of the stent 150.

Figure 4:
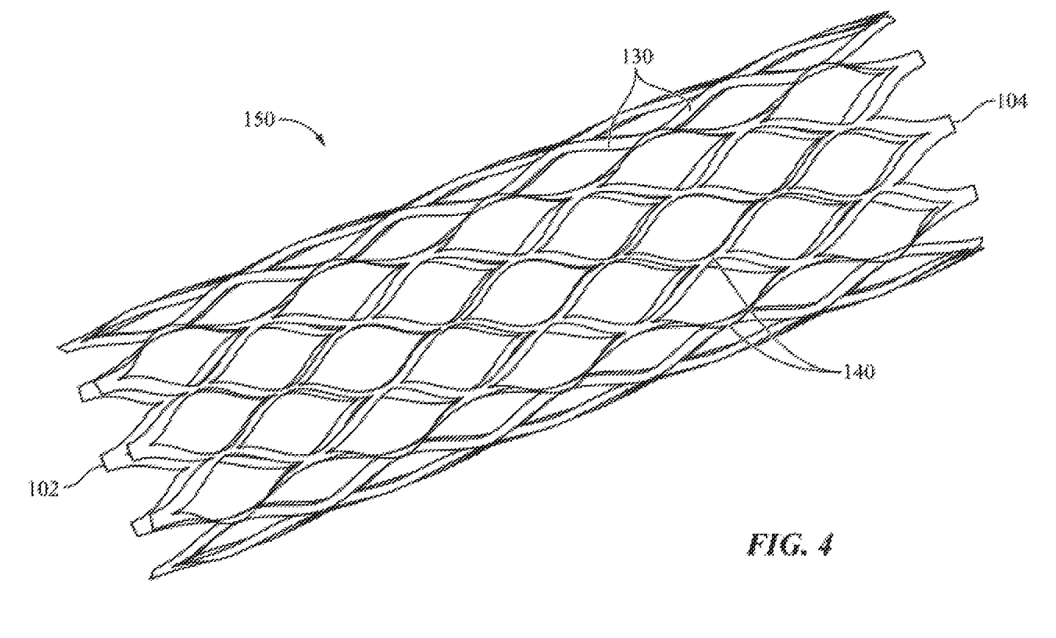
FIG. 4 is a perspective view showing the stent of FIG. 3 in its radially contracted configuration.

Illustrated in FIG. 4 is a collapsed state or configuration of the stent 150 shown in FIG. 3. More particularly, the collapsed state of the stent 150 is dimensioned for delivery through the body passage/lumen, for example on a guidewire where the stent has an outer dimension or diameter that allows the stent to move freely through the body passage/lumen to a desired site. To transform the stent 150 of FIG. 3 to the configuration illustrated in FIG. 4 can be accomplished in a variety of ways. One preferred manner is to place the tubular, thin-walled perforated structure of the stent 150 of FIG. 3 into a substantially flexible tube-referenced in FIG. 3 by broken line 160. Stretching the flexible tube 160 in the axial direction results in a reduction of the cross-sectional diameter of the tube. This reduction in the dimension of the tube 160, in turn, contracts the stent 150 in a uniform, axisymmetric manner. Controlling the amount of reduction of the cross-sectional diameter of the tube 160 controls the final collapsed dimension of the stent 150 shown in FIG. 4. Again, it will be recognized that this collapsed dimension will be selected in order to allow the stent 150 to be advanced through the body passage/lumen.

Figure 5:
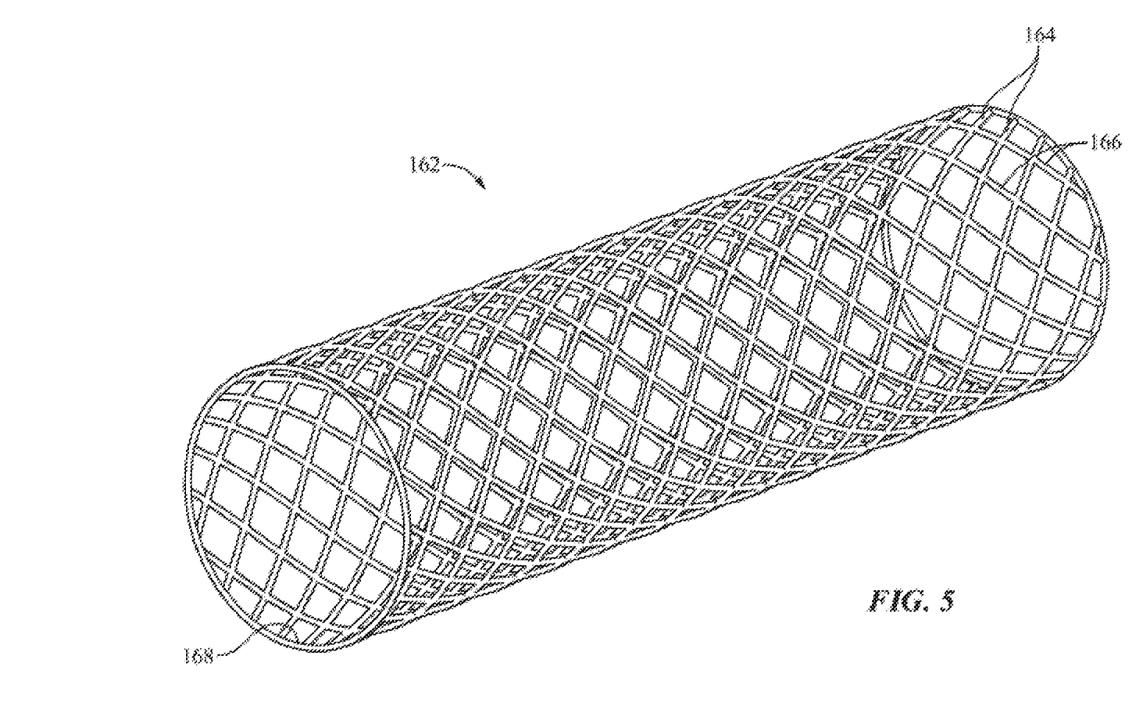
FIG. 5 is a perspective view of a truss dimensioned for receipt over and used to reduce the cross-sectional dimension of the stent of FIG. 3.

An alternative method is to use a custom-sized "Chinese finger trap" truss 162 that has a tubular configuration (FIG. 5). The truss 162 includes warp and weft strands 164, 166 that are normally arranged in an angled, overlapping configuration. When the strands 164, 166 are re-oriented into more closely linearly aligned relationship with one another by imposing a tensile force on the opposite ends of the truss 162, the inner opening 168 of the truss is reduced in cross-sectional dimension. Thus, the truss 162 of FIG. 5 is received over the stent shown in FIG. 3. The axial or longitudinal force imposed on opposite ends of the truss 162 elongates and/or stretches the truss resulting in a corresponding reduction in the internal diameter 168 of the truss which uniformly, axisymmetrically reduces the dimension of the stent 150 from the expanded configuration of FIG. 3 to the collapsed state of FIG. 4. The irregular shape of the links/struts 130 and interconnecting regions 140 in FIG. 4 relative to those shown in FIG. 3 are merely representative of a change in configuration of the struts as a result of the transition from the expanded state to the collapsed state. That is, the links/struts 130 need not adopt a determined conformation but the drawing merely illustrates that the links/struts are collapsed into an irregular configuration. Likewise, the irregular shape of the openings 120 is merely representative of this change from the expanded state/configuration to the collapsed state/configuration. Just as a metal mesh in a prior art arrangement can be easily expanded and deployed as a result of expanding, inflating a balloon so, too, is the mesh body of the present invention able to be reduced in dimension from the expanded state of FIG. 3 to the collapsed state of FIG. 4.

The inner and outer surfaces 134, 132, of links/struts 130 and inner and outer surfaces 144, 142 of the interconnecting regions 140 in the expanded state of FIG. 3 define a smooth contour that promotes smooth, laminar flow and reduces the potential of causing turbulence associated with the introduction of the stent 150 into the body passage. This is in direct contrast to a prior art arrangement where the links/struts and the corresponding interconnecting regions result in an out of plane, undesired twist in the individual links/struts in the expanded state. The twist in the prior art struts creates local blood-flow turbulences that may have adverse effects on the blood cells.

Once located at the desired location, the stent 150 of the present invention is expanded to the enlarged, deployed state shown in FIG. 3. Details with regard to deploying the stent 150, for example by using a balloon that is inflated and expanded in order to enlarge or expand the collapsed stent of FIG. 4 to the configuration shown in FIG. 3, are well known in the art and need not be shown and described herein for a complete understanding of the present invention. Once expanded, the links/struts 130 and interconnecting regions 140 are oriented in plane, i.e. in the curved surface and without any twist, which reduces the potential for turbulent blood flow through the deployed stent 150.

In another embodiment, the stent 150 can be initially fabricated in its contracted state; however, the individual links/struts 130 will be fabricated with a predetermined level of twisting. In this manner, when the stent 150 with twisted links/struts 130 is expanded, the twists will straighten out, i.e. vanish, and result in a smooth-surface configuration of the stent in its expanded state. In this embodiment, there is no need to collapse the stent 150 from an expanded state to a collapsed state, and subsequently re-expanding the stent again. Instead, fabrication of the stent 150 can proceed from a reduced dimension or small-diameter body with a predetermined level of twist in the individual links/struts 130 of the collapsed configuration of the stent 150 (FIG. 4), and the expanded state of the stent will adopt the configuration shown in FIG. 3 with the twist removed from the individual links/struts. Stated another way, because the links/struts 130 are not distorted in the enlarged or expanded configuration of FIG. 3, a maximum thickness of the stent wall measured from an innermost surface of an inner surface 134 of a link/strut or an inner surface 144 of an interconnecting region 140 to an outermost surface (or any outer surface 132 of a link/strut or an outer surface 142 of an interconnecting region 140) in the enlarged/expanded configuration is less than a maximum thickness of the stent wall (again, measured in the same manner) in the collapsed configuration of FIG. 4 because the links/struts and/or interconnecting regions are distorted and protrude either radially inwardly or outwardly from other links/struts in FIG. 4 and thus necessarily define a greater stent wall thickness in FIG. 4 (collapsed state) than in FIG. 3 (expanded state).

Figure 6:
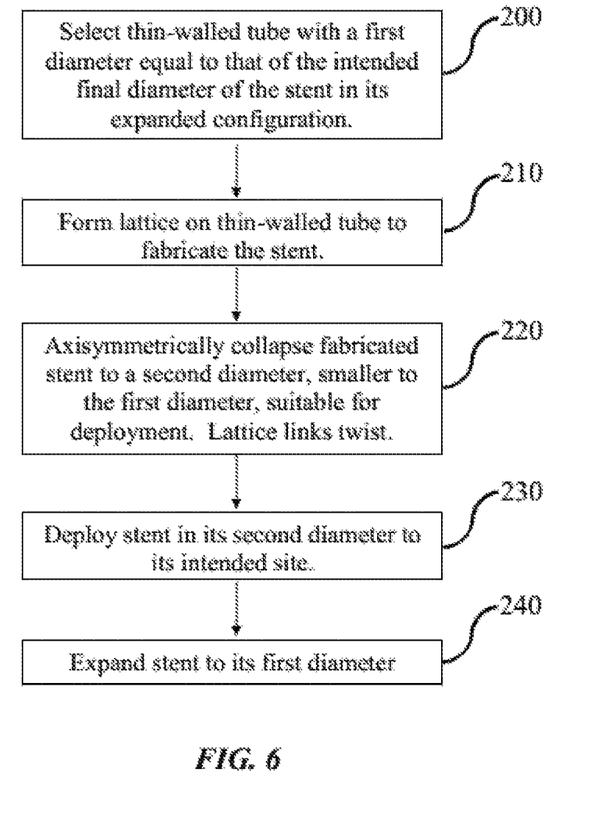
FIG. 6 is a flow chart outlining a preferred fabrication method.

In FIG. 6, select method steps are outlined to fabricate a first embodiment of the stent 150. In step 200, a thin-walled tube is selected or provided where the tube has a first outer surface dimension or diameter equal to that of the intended final dimension or diameter of the stent in its expanded configuration. Subsequently, the lattice is formed in the thin-wall tube to fabricate the stent as represented in step 210. Next, the fabricated stent is collapsed, preferably axisymmetrically collapsed, to a second dimension or diameter that is smaller than the first dimension or diameter. When collapsed, the lattice links or struts 130 twist. In the collapsed condition, the stent is delivered to the intended or desired site in the body passage (step 230). Thereafter, the stent 150 is expanded to the first dimension/diameter as noted in step 240.

Figure 7:
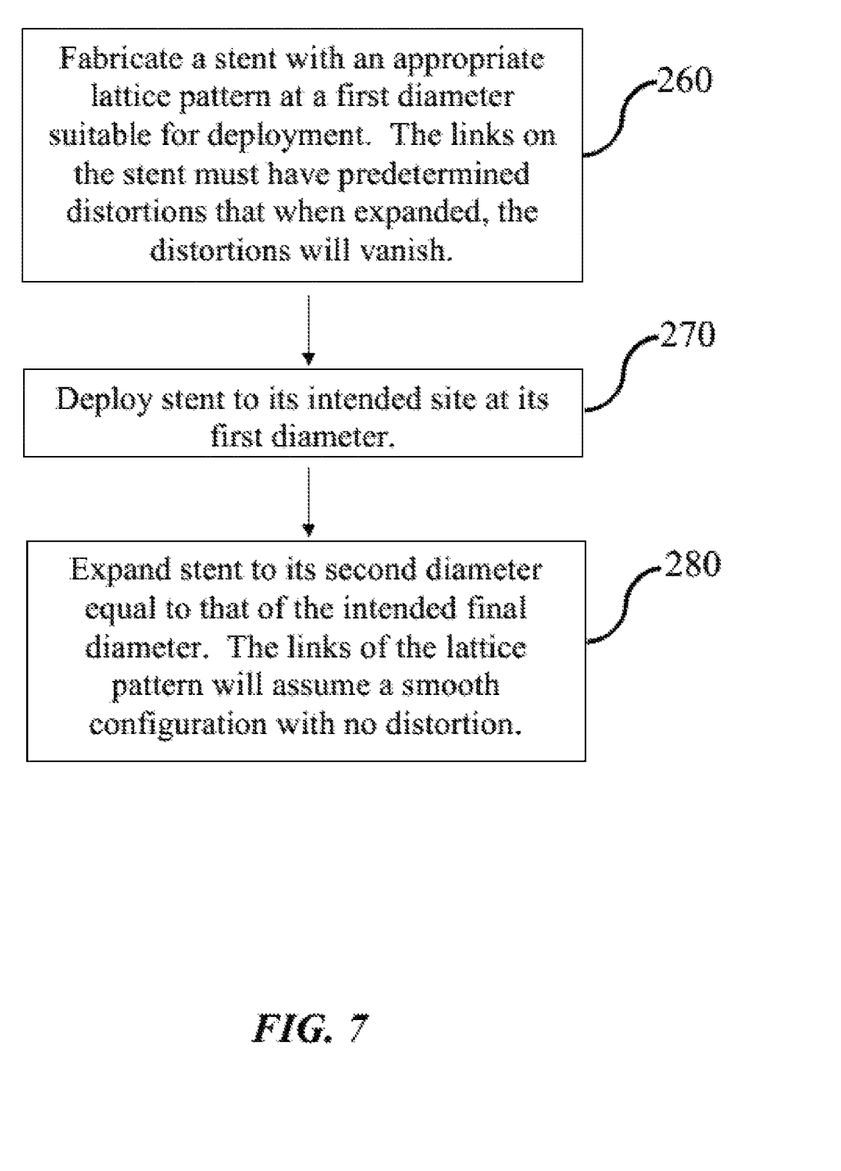
FIG. 7 is a flow chart outlining another preferred method of fabrication of the stent.

In FIG. 7 the following stent fabricating steps are outlined. In step 260, the alternative process includes initially selecting a stent 150 with a first dimension suitable for delivery in a collapsed state where the links/struts 130 on the stent have predetermined distortions. The stent 150 in the collapsed state is delivered to the intended or desired site (step 270). The lattice or mesh-like structure is then expanded to the second, enlarged dimension/diameter equal to that of the intended final dimension/diameter of the stent 150 in step 280. The links/struts 130 of the lattice pattern will assume a smooth configuration without distortion in the second state.

In summary, a thin wall tubing shown by numeral reference 100 has an outer diameter equal to that of the stent 150 in its fully expanded configuration as shown in FIG. 1. The thin wall tubular body 100 has struts that form a lattice of cylindrical coaxial hoops that are equally sized, and that are interconnected in an axial direction by axial strut portions or links. The interconnecting coaxial hoops serve to constrain the diameter wherein the stent can no longer be physically expanded beyond the diameter of the uncut tubular structure. A lattice mesh is then cut through the wall thickness f this tube 100 with the result shown in FIG. 2. The removed material leaves an opening(s) 120 and a typical stent structural strut/link 130 as shown in FIG. 2. FIG. 3 shows the fully formed stent 150 in its fully expanded configuration with not twist or distortion of the strut/links 130. FIG. 4 shows the stent 150 when it is radially contracted, assuming an outer diameter smaller than its original expanded configuration. As a result of contraction, the individual links of the stent undergo an out of plane twisting; FIG. 4 shows the stent in its collapsed state and prior to its deployment through the vascular lumen to be placed at a desirable site. When the stent of FIG. 4 is expanded radially to its fully expanded configuration (original tube diameter of FIG. 1), the out of plane twisting of individual struts/links 130 will disappear on the stent 150, and the stent will assume the fully expanded configuration having a smooth outer surface as depicted in FIG. 2.

This written description uses examples to describe the disclosure, including the best mode, and also to enable any person skilled in the art to make and use the disclosure. Other examples that occur to those skilled in the art are intended to be within the scope of the invention if they have structural elements that do not differ from the same concept, or if they include equivalent structural elements with insubstantial differences.

What is claimed is:

1. A method of fabricating an intravascular stent comprising:
   providing a thin wall tube having a cylindrical wall formed around a longitudinal axis, the wall having a first, outer dimension equal to that of a fully expanded configuration of the intravascular stent;
   removing material from the wall to form geometric patterns through the wall, leaving an interconnected lattice including forming annular, circumferentially continuous struts and longitudinal struts extending perpendicular thereto, the annular struts having a continuous first end face defined in a first cross-sectional plane perpendicular to the longitudinal axis and a second end face defined in a second cross-sectional plane perpendicular to the longitudinal axis wherein the first and second end faces are axially spaced a uniform dimension from each other where the struts have circular outer surfaces and circular inner surfaces forming an internal through passage that proceeds continuously from a proximal end to a distal end of the tube, and the circular outer surfaces have an outer diameter equal to the first, outer dimension of the tube wall;
   radially contracting the stent to a contracted configuration by uniformly and axisymmetrically reducing a cross-sectional dimension of the tubular body, and wherein the annular and longitudinal struts are not perpendicular to one another and form a second, smaller collapsed dimension for storage, delivery, and subsequent deployment;
   expanding the contracted configuration of the stent to its original, fully expanded configuration where the circular outer surfaces of the struts are expanded so that the circular outer surfaces thereof are expanded to the first, outer dimension when positioned at a desired site in the vascular lumen; and
   wherein the stent retains its radial structural integrity and has no out of plane twisting after the expanding step when the stent is configured to its original, fully expanded configuration.

2. The method of claim 1 wherein the contracting step includes placing the stent in a flexible tube and reducing the dimension of the flexible tube in order to contract the stent therein.

3. The method of claim 1 wherein the contracting step further includes placing the stent in a truss structure that when axially stretched, shrinks the stent in the axisymmetric, uniform fashion to its contracted configuration.

4. The method of claim 1 further comprising forming the lattice with individual twisted links in the contracted configuration and removing the twist in the links in the expanded configuration.

5. The method of claim 1 wherein the thin wall tube providing step includes having cylindrical coaxial struts all having the same radial outer surface dimension.

6. The method of claim 1 wherein the thin wall tube providing step further includes interconnecting the coaxial hoops that form a lattice.

7. The method of claim 1 further comprising forming interconnecting coaxial struts where each strut has an outer surface diameter equal to the outer dimension of the tubular body wall.

8. A method of fabricating a stent comprising:
forming a uniform lattice arrangement that includes a series of struts and openings in a wall of a tubular body, including forming annular, circumferentially continuous struts and longitudinal struts extending perpendicular thereto, the annular struts having a continuous first end face defined in a first cross-sectional plane perpendicular to the longitudinal axis and a second end face defined in a second cross-sectional plane perpendicular to the longitudinal axis wherein the first and second end faces are axially spaced a uniform dimension from each other, where the struts have circular outer surfaces having an outer diameter equal to an outer dimension of the tubular body wall;
reducing a cross-sectional dimension of the tubular body by uniformly and axisymmetrically contracting the tubular body to the reduced dimension and providing a collapsed state of the tubular body where the annular and longitudinal struts are not perpendicular to one another and form a distorted configuration and an expanded state of the tubular body wherein the distorted configuration of the struts vanishes and the outer diameters of the struts are equal to the outer dimension of the tubular body wall, wherein the lattice is formed in a tubular body that has a dimension that is the same as the expanded state; and
wherein the stent retains its radial structural integrity and has no out of plane twisting when configured to the expanded state and the original, fully expanded configuration.

9. The method of claim 8 including expanding the tubular body to an enlarged dimension for securing the stent in the associated body passage.

10. The method of claim 8 including surrounding the tubular body in a sleeve and reducing a cross-sectional dimension of the sleeve and uniformly deforming the tubular body to the reduced dimension.

11. A method of fabricating a stent comprising:
forming a lattice arrangement that includes a series of struts and openings in a wall of a tubular body, providing annular, circumferentially continuous struts and longitudinal struts extending perpendicular thereto, the annular struts having a continuous first end face defined in a first cross-sectional plane perpendicular to the longitudinal axis and a second end face defined in a second cross-sectional plane perpendicular to the longitudinal axis wherein the first and second end faces are axially spaced a uniform dimension from each other, the annular struts having circular outer surfaces having an outer diameter equal to an outer dimension of the tubular body wall;
reducing a cross-sectional dimension of the tubular body by uniformly and axisymmetrically contracting the tubular body to the reduced dimension and providing a collapsed state of the tubular body where the annular and longitudinal struts are not perpendicular to one another and forms a distorted configuration;
providing an expanded state of the tubular body that is no greater than the wall of the tubular body, such that in the expanded state all radial outer surfaces of the struts lie in an outer perimeter cylindrical surface portion of a virtual, continuous cylinder having the first, outer dimension; and
wherein the stent retains its radial structural integrity and has no out of plane twisting when configured to the expanded state and the original, fully expanded configuration.

12. The method of claim 11 including forming the lattice arrangement in a tubular body that has a dimension that is the same as the expanded state.

13. The method of claim 11 including collapsing the tubular body to a reduced dimension for delivery of the stent through an associated body passage.

14. The method of claim 11 including expanding the tubular body to an enlarged dimension for securing the stent in the associated body passage.

15. The method of claim 11 including surrounding the tubular body in a sleeve and reducing a cross-sectional dimension of the sleeve and uniformly deforming the tubular body to the reduced dimension.

16. The method of claim 11 wherein the distorted configuration of the struts vanishes in the expanded state of the tubular body.

* * * * *